(12) United States Patent
Zhang et al.

(10) Patent No.: US 10,744,109 B2
(45) Date of Patent: Aug. 18, 2020

(54) SUSTAINED RELEASE SUSPENSION CONTAINING DEZOCINE ANALOGUE ESTER AND PREPARATION METHOD THEREFOR

(71) Applicant: SHANDONG DANHONG PHARMACEUTICAL CO., LTD., Shandong (CN)

(72) Inventors: Yang Zhang, Shanghai (CN); Bing Deng, Shanghai (CN); Jiahu Wu, Shanghai (CN); Wentao Wu, Shanghai (CN); Zhixiang Li, Shanghai (CN)

(73) Assignee: SHANDONG DANHONG PHARMACEUTICAL CO., LTD., Shandong (CN)

( * ) Notice: Subject to any disclaimer, the term of this patent is extended or adjusted under 35 U.S.C. 154(b) by 0 days.

(21) Appl. No.: 16/607,685

(22) PCT Filed: Aug. 7, 2018

(86) PCT No.: PCT/CN2018/099232
§ 371 (c)(1),
(2) Date: Oct. 23, 2019

(87) PCT Pub. No.: WO2019/007441
PCT Pub. Date: Jan. 10, 2019

(65) Prior Publication Data
US 2020/0188342 A1      Jun. 18, 2020

(30) Foreign Application Priority Data
Jul. 4, 2017   (CN) .......................... 2017 1 0539419

(51) Int. Cl.
*A61K 31/215*    (2006.01)
*A61K 9/10*      (2006.01)
*A61K 9/00*      (2006.01)
*A61K 47/44*     (2017.01)

(52) U.S. Cl.
CPC .......... *A61K 31/215* (2013.01); *A61K 9/0019* (2013.01); *A61K 9/10* (2013.01); *A61K 47/44* (2013.01)

(58) Field of Classification Search
None
See application file for complete search history.

(56) References Cited

U.S. PATENT DOCUMENTS 10,414,718 B2 *   9/2019   Zhang ................... C07C 215/64
2019/0010114 A1   1/2019   Zhang

FOREIGN PATENT DOCUMENTS

| CN | 104274473 A | 1/2015 |
|---|---|---|
| CN | 104523584 A | 4/2015 |
| CN | 104622803 A | 5/2015 |
| EP | 2949316 A1 | 12/2015 |
| WO | 2012066347 A1 | 5/2012 |
| WO | 2017118375 A1 | 7/2017 |

OTHER PUBLICATIONS

Structures for U.S. Appl. No. 16/607,685; drawn in and uploaded from ChemDraw May 7, 2020.*
SciFinder search results for fluroinated dezocine; uploaded May 7, 2020.*
SciFinder search results for Formula (I) of claim 1 of U.S. Appl. No. 16/607,685; uploaded May 7, 2020.*
International Search Report and Written Opinion of PCT/CN2018/099232 dated Oct. 17, 2018.
International Search Report and Written Opinion of PCT/CN2018/103854 dated Nov. 20, 2018.
English translation of Chinese priority application No. 201710539419.8.
Extended European Search Report in corresponding European Application No. 18828904.5 dated Apr. 30, 2020, 8 pages.

* cited by examiner

*Primary Examiner* — Jeffrey T. Palenik
(74) *Attorney, Agent, or Firm* — MH2 Technology Law Group LLP

(57) ABSTRACT

Disclosed are a sustained release suspension containing dezocine analogue ester and a preparation method therefor. According to the present invention, an injectable oily auxiliary material which may pharmaceutically serve as a sustained-release depot and an excipient are selected, and micronization technology is used jointly with high pressure homogenization technology and an anti-solvent technique to prepare an injectable long-acting suspension. The main components of the suspension are a compound represented by formula (I), the injectable oil, and the like.

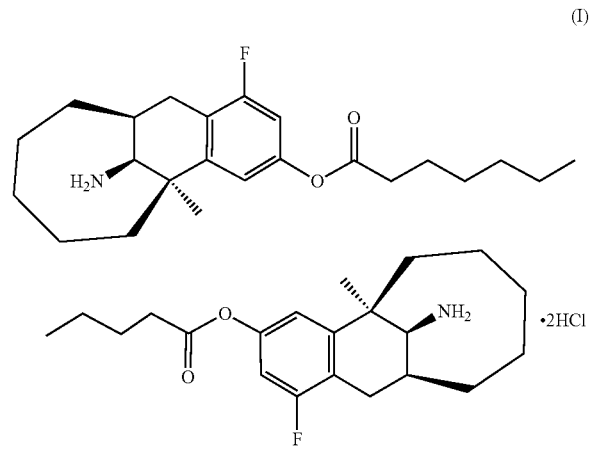

12 Claims, 1 Drawing Sheet

SUSTAINED RELEASE SUSPENSION CONTAINING DEZOCINE ANALOGUE ESTER AND PREPARATION METHOD THEREFOR

CROSS REFERENCE TO RELATED APPLICATION

The present application is a national stage entry under 35 U.S.C. § 371 of PCT Application No. PCT/CN2018/099232 filed on Aug. 7, 2018, which claims the priority of the Chinese Patent Application CN201710539419.8 filed on Jul. 4, 2017, the contents of both of which are incorporated herein in the present application.

FIELD OF INVENTION

The present invention relates to pharmaceutical field, specifically to an analgesic oily sustained release suspension containing a compound as shown in formula (I) and a preparation method thereof.

PRIOR ARTS

The compound as shown in formula (I) is a sebacic acid diester prodrug of a compound as shown in formula (II), a dezocine analogue, which is unstable in plasma and can release the active compound as shown in formula (II) after hydrolysis in vivo.

The compound as shown in formula (I) has a low solubility in both water and oil solution, which is slightly soluble in water and hardly soluble or insoluble in oil solution. Further, the compound as shown in formula (I) has a short half-life and the clearance rate of which is too fast to achieve a sustained release effect in vivo when prepared as an aqueous solution.

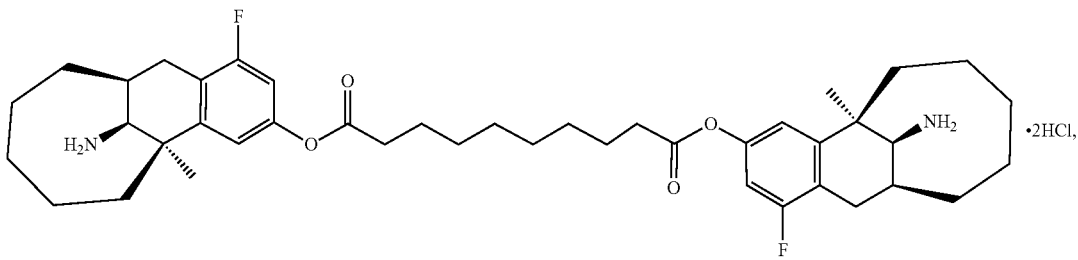

(I)

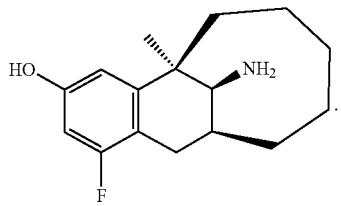

(II)

TECHNICAL EFFECT

The suspension injection preparation of the present invention is of simple composition, stable property, simply prepared, and is suitable for large-scale production, research and development. Moreover, the suspension has the advantages of low viscosity, good settling ratio, redispersibility, excellent syringeability and so on.

CONTENT OF THE PRESENT INVENTION

On an aspect, the present invention provides a sustained release suspension containing a compound as shown in formula (I), an injectable oil and an excipient,

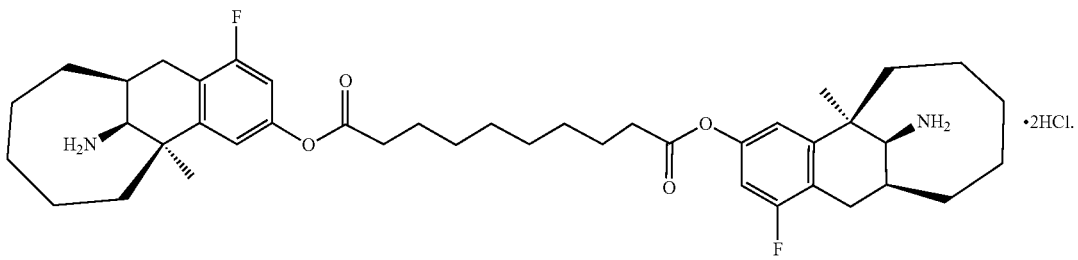

(I)

In some embodiments of the present invention, the content of the compound as shown in formula (I) in the sustained release suspension is 5-20 wt. %.

In some embodiments of the present invention, the content of the excipient in the sustained release suspension is 0.25-2 wt. %.

In some embodiments of the present invention, the content of the injectable oil in the sustained release suspension is 80-95 wt. %.

In some embodiments of the present invention, the injectable oil is selected from the group consisting of medium chain triglycerides, soybean oil, olive oil, sesame oil, corn oil, cottonseed oil, isopropyl myristate and a mixture thereof.

In some embodiments of the present invention, the excipient is selected from the group consisting of wetting agent and suspending agent.

In some embodiments of the present invention, the wetting agent is selected from the group consisting of Tween 80, RH40, PEG400, poloxamer 188, HS-15, ethanol, propylene glycol, Span 80, polyoxyethylene hydrogenated stearate, polyoxyethylene castor oil and derivatives thereof.

In some embodiments of the present invention, the suspending agent is selected from the group consisting of methylcellulose, PVP, gelatin, sodium alginate, aluminum stearate and aluminum tristearate.

On another aspect, the present invention provides a method for preparing the sustained release suspension, which adopts a highly dispersing method.

In some embodiments of the present invention, the highly dispersed method is selected from the group consisting of a micronization method, an anti-solvent method, a high pressure homogenization method and a pre-suspension method.

In some embodiments of the present invention, 90% of the particle obtained by the method is of a particle diameter ≤15 μm.

DEFINITION AND DESCRIPTION

Unless otherwise indicated, the following terms and phrases when used in the present invention have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The intermediate compound of the present invention can be prepared by a variety of synthetic methods well known to the skilled in the art, including the following enumerative embodiment, the embodiment formed by the following enumerative embodiment in combination with other chemical synthetic methods and the alternatives well known to the skilled in the art, the preferred embodiments include, but are not limited to the embodiments of the present invention.

The chemical reaction of the enumerative embodiment of the present invention is carried out in a suitable solvent which is suitable for the chemical conversion of the present invention and the reagents and materials required thereof. In order to obtain the compounds of the present invention, sometimes it requires one skilled in the art to modify or select the synthetic steps or reaction schemes based on the given embodiments.

The following embodiments further illustrate the present invention, but by all means the invention is not limited thereto.

All of the solvents used in the present invention are commercially available and can be used without further purification.

The solvents used in the present invention are commercially available.

Herein the abbreviations are as follows:

RH40: polyoxyethylene 40 hydrogenated castor oil
PEG400: polyethylene glycol 400
HS-15: polyethylene glycol 15 hydroxystearic acid
PVP: polyvinylpyrrolidone
RH: relative humidity
wt. % weight percentage Apparatus and Analysis Methods 1. Main Apparatus and Parameters Used in the Preparation Method are as Shown in Table 1.

TABLE 1

|  | Apparatus type | Parameter |
| --- | --- | --- |
| High-pressure homogenizer | FSY001-0707 | 6000 psi for 5 cycles<br>3000 psi for 5 cycles<br>Pipe temperature controlled at 0 to −20° C. |
| Pulverizer | ZL-R100 | Pressure: 0.78 Mbar<br>feeding speed: 1 kg/h |
| Agitator (high-speed homogenizer) | Digital T25 | 10000 rpm for 1 minute |

2. Test for Settling Ratio of the Suspension:

The suspension was dispensed into a 50 mL measuring cylinder and shaken for one minute to mix uniformly, left at room temperature, the original height marked as H0 before sedimentation was recorded, and the sedimentation height H was recorded after 1 hr, 2 hrs and 3 hrs respectively, and the settling ratio was calculated according to the formula F=H/H0.

Apparatus: measuring cylinder, ruler

3. Test for Particle Size and Particle Size Distribution of the Suspension:

Apparatus Type: Microtrac-X100 Particle Size Distribution Analyzer (PSD)

Test conditions: an appropriate amount of the substance to be tested was placed into a sample bottle, and the dispersion medium (isoparaffin solvent containing 0.25% lecithin) was added, and the mixture was uniformly mixed by manual and then added to the sample cell to test the sample. The detailed PSD parameters were as shown in Table 2 below (wet method):

TABLE 2

| Measuring range | Lens: 0.122~704.0 μm | |
| --- | --- | --- |
| Test setup | Blank background test time: 30 s<br>Duplicated times: 3 times<br>Dispersing liquid refractive index: 1.42 (Isopar G)<br>Particle refractive index: 1.51 | Sample test time: 10 s<br>Filter: on<br>Particle shape: irregular<br>Particle transparency: transparent |
|  | Over-range processing function: activated | Particle size measurement range expansion: off |
| Disperser | Type: ASVR<br>Ultrasonic power: 20 w | Cycling rate: 60%<br>Ultrasonic time: 30 s |

4. Polarized Microscope (PLM) Experimental Protocol
Polarized Light Microscope (PLM)
Apparatus type: Nikon LV100 polarizing microscope
Test method: The sample was placed on a glass slide and observed after dispersed with the silicone oil. Eyepiece: 10 times, objective lens: 20/50 times.

5. Test Protocol for Suspension Content:
5.1 Equipment Type:
High performance liquid phase detector (Agilent 1260 PDA Detector)
Column: Kromasil C18 (4.6×250 mm, 5 μm)
5.2 Chromatographic Conditions
Mobile phase A: 0.05% trifluoroacetic acid aqueous solution, mobile phase B: 0.05% trifluoroacetic acid in acetonitrile; column temperature: 35° C.; flow rate: 1 mL/min; detection wavelength: 215 nm; sample solution concentration: 0.08 mg/mL, sample size: 50 μL;
The gradients were as shown in Table 3 below:

TABLE 3

| Time | Mobile phase B (%) |
|---|---|
| 0.01 | 20 |
| 30.00 | 98 |
| 40.00 | 98 |
| 40.01 | 20 |
| 60.00 | Stop |

5.3 Preparation of the Solution to be Tested
A sample of the preparation (specification: 1 mL, 50 mg) was shaken thoroughly, and then transferred to a 5 mL centrifuge tube, and 3 mL acetonitrile-water (2:1) solution was measured accurately, and rinsed the inner wall of the preparation bottle in batches, the rinsing solutions were combined and poured into the centrifuge tube. After shaking uniformly, the sample underwent ultrasonic oscillation for 20 min (50% intensity), was shaken vigorously for 1 min (intensity 4) with a vortexer, and then placed in a centrifuge, centrifuged at 12000 rpm for 15 min, and the supernatant was drawn to the vial with a syringe. 1.5 mL The supernatant was measured accurately and placed into a 25 mL volumetric flask, and then diluted with acetonitrile-water (2:1) and set to scale; 2 mL of which was measured accurately and placed into 25 mL volumetric flask, and acetonitrile-water (2:1) was added to dilute and set to scale to obtain a solution to be tested with a concentration of about 0.08 mg/mL.

5.4 Preparation of Control Solution
10 mg control substance was weighed accurately, placed into a 25 mL volumetric flask, added with acetonitrile-water (2:1) solution to dissolve and dilute to the scale; 2 mL was measured accurately and added into a 10 mL volumetric flask, and added with acetonitrile-water (2:1) to dilute and set to scale to obtain a solution to be tested with a concentration of about 0.08 mg/mL.

6. Test Protocol for the Detection of the Substance Content Contained in the Suspension:
6.1 Equipment Type:
High performance liquid phase detector (Agilent 1260 PDA Detector)
Column: Kromasil C18 (4.6×250 mm, 5 μm);
6.2 Chromatographic Conditions
Mobile phase A: 0.05% trifluoroacetic acid aqueous solution, mobile phase B: 0.05% trifluoroacetic acid in acetonitrile; column temperature: 35° C.; flow rate: 1 mL/min; detection wavelength: 215 nm; sample solution concentration: 0.08 mg/mL, sample size: 10 μL;

The gradient program was shown in Table 4 below:

TABLE 4

| Time | Mobile phase B (%) |
|---|---|
| 0.01 | 20 |
| 10.00 | 45 |
| 40.00 | 100 |
| 50.01 | 100 |
| 50.00 | 20 |
| 60.00 | 20 |

The preparation method of the solution to be tested and the control solution were the same as those of the solution to be tested and the control solution recited in 5.3 and 5.4 respectively.

Scheme 1

Figure 1:
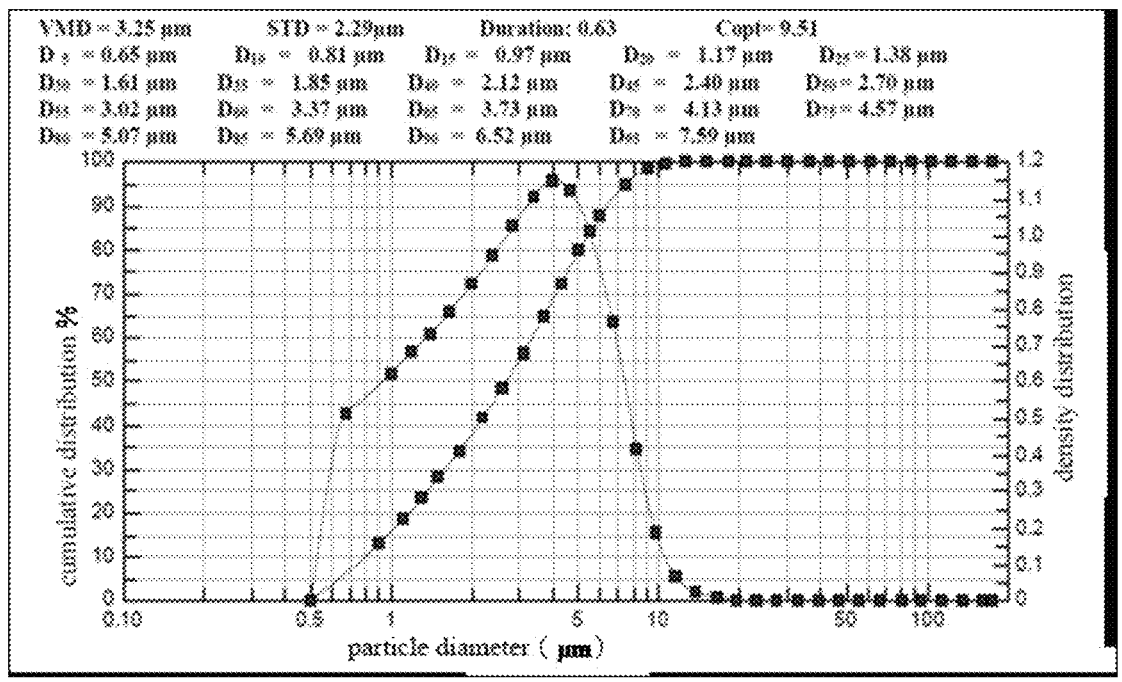
FIG. 1 is the particle size distribution of the suspension obtained according to embodiment 4.

In the preparation of an oily suspension injection of the compound as shown in formula (I), every 10 mL of the oily suspension injection includes:
the compound as shown in formula (I): 0.5 g
injectable oil: 8 g
suspending agent: 0.5-4%
wetting agent: 0.2-0.6%
the injectable oil is selected from the group consisting of medium chain triglyceride, soybean oil, olive oil, sesame oil, corn oil, cottonseed oil and isopropyl myristate. Medium chain triglyceride or soybean oil was preferred.
The suspending agent is selected from the group consisting of aluminum stearate, aluminum tristearate, methylcellulose, PVP, gelatin and sodium alginate. Aluminum stearate or aluminum tristearate was preferred.
The wetting agent is selected from the group consisting of Tween 80, RH40, PEG400, poloxamer 188, HS-15, ethanol, propylene glycol, Span 80, polyoxyethylene hydrogenated stearate and polyoxyethylene castor oil. Tween 80 or RH40 was preferred.
A method for preparing the oily suspension injection of the compound as shown in formula (I) can employ a dispersing method, and the specific steps are as follows:
1. weighing the injection oil accurately, adding with the suspending agent, and stirring at room temperature for 1 hour, being heated to 120° C. and stirred for 3 hours, then taken away from heating, and kept stirring till the injection oil cooled to room temperature, and being reserved.
2. weighing the oil solution obtained in step 1 accurately, adding with the wetting agent at 60° C., being stirred at high speed (2500 rpm) for 5 minutes. The compound as shown in formula (I) was weighed accurately based on the prescription, and then slowly added to the high-speed stirring oil by means of adding a small amount at a time. The suspension injection was obtained by maintaining the solution for 1 hour.

Scheme 2

In the preparation of an oily suspension injection of the compound as shown in formula (I), every mL of the oily suspension injection includes:
the compound as shown in formula (I): 0.05 g
injectable oil: 0.947 g A long-acting oily suspension injection of the compound as shown in formula (I) can employ a pre-suspension method, and the specific steps are as follows:

1. pulverizing the powder of the compound as shown in formula (I) in a pulverizer to 90% particle being of a diameter ≤7 μm;
2. weighing 0.947 g injection oil and being placed into a 2 mL vial, sealed and sterilized;
3. treating and micronizing the compound as shown in formula (I) aseptically, and sub-packaging at 0.05 g per 2 mL vial in a sterile environment;
4. upon use, injecting the sterilized oil into the vial obtained according to step 3 and the suspension was obtained by manually mixing.

Scheme 3

In the preparation of an oily suspension injection of the compound as shown in formula (I), every 10 mL of the oily suspension injection includes:
the compound as shown in formula (I): 0.5 g
injectable oil: 9.47 g
wetting agent: 0.2-0.6%

A method for preparing the oily suspension injection of the compound as shown in formula (I) can employ high pressure homogenization, and the specific steps are as follows:

1. pulverizing the powder of the compound as shown in formula (I) in a pulverizer to 90% particle being of a diameter ≤7 μm;
2. adding an appropriate amount of a surfactant to the injectable oil, heating at 60° C. and stirring for 30 minutes;
3. adding the oil obtained according to step 2 to the powder of the compound as shown in formula (I) obtained according to step 1 and stirring at 10,000 rpm for 1 minute by using a high-speed homogenizer to completely disperse and form a suspension;
4. ultra-fine processing the suspension obtained according to step 3 in a high-pressure homogenizer to obtain the suspension injection;
5. Sub-packaging the suspension injection obtained according to step 4 into coated vials, being sealed with a coated rubber plug and an aluminum cap, and then placed in a moist heat sterilizer for terminal sterilization.

The high pressure homogenization process described in step 4 specifically includes the following steps:
a) homogenizing under 6000 psi for 5 cycles;
b) homogenizing under 3000 psi for 5 cycles; wherein the pipe temperature during homogenization is controlled between 0 and −20° C.

The present invention provides three methods for preparing an oily suspension injection of the compound as shown in formula (I). Since the oily suspension generally has the characteristics of easy sedimentation, the present invention adopts three preparation methods, and according to the sedimentation property of the suspension, the stability of the suspension is increased by increasing the viscosity of the suspension, reducing the particle size of the drug, and pre-mixing and sub-packaging methods. These three preparation methods are simple, the auxiliary materials are cheap and easy to be obtained, and the obtained preparation has stable performance which meets the requirements of the Pharmacopoeia, can be industrialized, and has a promising prospect.

DETAILED DESCRIPTION OF THE PREFERRED EMBODIMENTS

The following embodiments further illustrate the present invention, but by all means the invention is not limited thereto. While the present invention has been described in detail and with reference to specific embodiments thereof, it will be apparent to those skilled in the art that various changes and modifications can be made therein without departing from the spirit and scope thereof.

Embodiment 1

1. Medium chain triglyceride was weighed by 50 g accurately, added with 0.4 g aluminum tristearate, and the mixture was stirred at room temperature for 1 hour, heated to 120° C. and stirred for 3 hours, and then stopped heating, and left to stir until the mixture was room temperature, reserved.

2. Oil solution obtained according to step 1 was weighed by 8.0 g and RH40 by 0.25 g accurately, and the mixture was stirred at high speed (2500 rpm) for 5 minutes at 60° C. The compound as shown in formula (I) was weighed by 3.125 g accurately, and then slowly added to the high-speed stirring oil with a small amount at a time, left for 1 hour to give the suspension.

The stability of the suspension obtained according to embodiment 1 under the conditions of strong light, high temperature and high pressure and the influence of the relevant substances were measured. The results were as shown in Table 5. The influencing factors showed that there was no significant increase in the relevant substances and no significant change in the particle size distribution. The settling ratio met the requirements of the Pharmacopoeia and the suspension was stable.

TABLE 5

Stability of the suspension obtained according to embodiment 1 and the content of the relevant substances

| Condition | Settling ratio | Viscosity | Particle diameter D90(μm) | Content of the relevant substances (%) | Dispersion property |
| --- | --- | --- | --- | --- | --- |
| Room temperature | 0.91 | Easily flow | 13.1 | 3.19 | easily dispersed |
| High temperature | 0.98 | Slight increase in viscosity | 16.0 | 3.55 | dispersible |
| Light | 0.90 | Easily flow | 14.2 | 3.57 | easily dispersed |
| High humidity | 0.92 | Easily flow | 15.0 | 3.56 | easily dispersed |

Embodiment 2

1. 50 g medium chain triglyceride, 0.15 g aluminum tristearate were weighed and the mixture was stirred at room temperature for 30 minutes, heated to 120° C. in an oil bath and stirred for 2 hours, the oil was dissolved to form a clear and transparent solution, then left till cool and reserved;

2. the compound as shown in formula (I) was weighed by 0.5 g, dissolved in 4 mL anhydrous ethanol, and conduct ultrasonic oscillation for 10 seconds to dissolve, reserved;

3. 10 mL oil phase obtained according to Step 1 was measured, placed in a 60° C. water bath, then stirred at a high speed (2400 rpm), and slowly added with a solution of the compound as shown in formula (I) in ethanol obtained according to step 2 dropwise, and the mixture was stirred openly for 1 hour to obtain the suspension injection;

TABLE 6

Characterization data of the suspension obtained according to embodiment 2

| Settling ratio | Viscosity | Particle diameter D90(μm) | Dispersion property |
|---|---|---|---|
| 0.95 | Easily flow | 13.1 | Easily dispersed |

The results showed that the settling ratio of the suspension after 3 hours was greater than 0.9 as required in the Pharmacopoeia, and the particle diameter also met the relevant requirements for the particle diameter of the suspension as required in the Pharmacopoeia.

Embodiment 3

1. Bottle 1: The Compound as Shown in Formula (I)

After micronized, the compound as shown in formula (I) was sub-packaged at 50 mg/mL per 2 mL vial.

2. Bottle 2: Diluent 100 mL medium-chain triglyceride was accurately measured, and added with 100 mg activated carbon for refinement of injection, and the mixture was stirred at 60° C. for 15 minutes, went through a 0.8 μm filter membrane, and then went through a 0.22 μm microporous membrane, and sub-packaged at 1.1 mL/bottle.

TABLE 7

Stability data of the suspension obtained in embodiment 3 after three months

| Condition | Re-dissolve | Content of the compound (%) | Content of the relevant substances (%) | Particle distribution D90(μm) | Content of water (%) |
|---|---|---|---|---|---|
| Room temperature | dispersible mixing | 97.12 | 2.16 | 11.32 | 3.28 |
| 60° C. evenly | uniformly | 92.43 | 5.91 | 11.86 | 4.12 |

From the results in Table 7, the content of the compound did not decrease significantly and the relevant substances did not increase significantly after being placed at room temperature for three months. The powder was able to be uniformly dispersed in the medium chain triglyceride and the particle diameter D90 (μm) was 11.32 μm which met the requirements of the Pharmacopoeia; however, at 60° C., the content decreased and the relevant substances increased significantly, but the drug powder could still be well dispersed. The above results showed that it has a great feasibility to prepare the suspension by premixing under the condition of controlling the storage temperature.

Embodiment 4

1. The powder of the compound as shown in formula (I) was pulverized in a pulverizer to 90% particle being of a particle diameter ≤7 μm;

2. 6.7 g Tween 80 was added to the injectable oil, and heated and stirred at 60° C. for 30 minutes;

3. 150.8 g powder of the compound as shown in formula (I) obtained according to step 1 was added to the oil obtained according to step 2 and stirred at 10,000 rpm for 1 minute by using a high-speed homogenizer to be completely dispersed and form a suspension;

4. The suspension obtained according to step 3 was subject to ultra-fine processing in a high-pressure homogenizer to obtain the suspension injection;

The high pressure homogenization process described in step 4 specifically includes the following steps:

a) homogenizing under 6000 psi for 5 cycles;

b) homogenizing under 3000 psi for 5 cycles; wherein the pipe temperature during homogenization is controlled between 0 and −20° C.

5. The suspension injection obtained according to step 4 was sub-packaged into coated vials, sealed with a coated rubber plug and an aluminum cap, and placed in a moist heat sterilizer for terminal sterilization.

Figure 2:
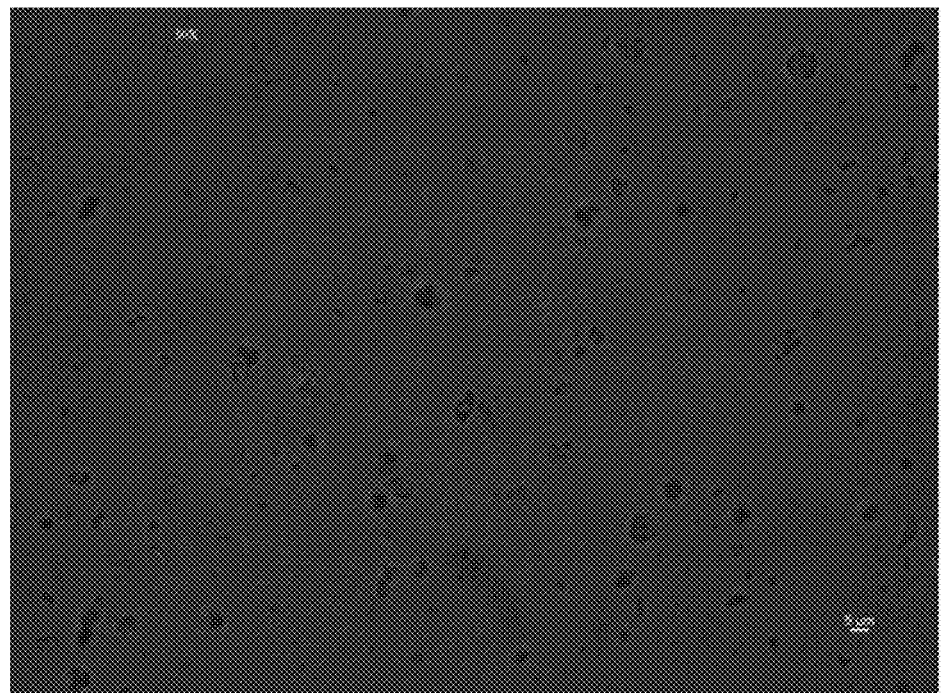
FIG. 2 is the PLM micrograph of the suspension obtained according to embodiment 4.
In order to achieve the above technical effects, embodiments of the present invention are as follows.

The suspension obtained in embodiment 4 was characterized, including particle diameter detection, polarized light microscopy (PLM), settling ratio, viscosity, redispersibility and syringeability. The particle size distribution and PLM micrographs of the suspension obtained in embodiment 4 were as shown in FIGS. 1 and 2.

TABLE 8

Characterization data of the suspension obtained in embodiment 4

| Settling ratio | Viscosity | Particle distribution D90(μm) | Dispersion property | Syringeability |
|---|---|---|---|---|
| 1 | Easily flow | 14.1 | Easily dispersed | capable of passing through specification 27 |

The stability of the suspension obtained in embodiment 4 under different accelerated conditions and the influence of relevant substances were measured, which were shown in Table 9. The results regarding the stability of the suspension of embodiment 4 showed that the particle diameter under three conditions did not change significantly after being placed for two months, and the results regarding settling ratio showed that the stability of the suspension material was very good, and at the same time, the results regarding the relevant substances showed that there was no significant increase in these two months. The above results showed that the overall stability of the suspension in embodiment 4 was good.

TABLE 9

Stability of the suspension obtained in embodiment 4 after 2 months

| Time | Condition | Particle distribution D90(μm) | Content of the compound (%) | Content of the relevant substances (%) | Dispersion property | Settling ratio |
|---|---|---|---|---|---|---|
| 0 day | 25° C./60% RH | 11.7 | 94.1 | 3.47 | Dispersible | 1 |
| 60 day | 2-8° C. | 12.1 | 95.1 | 3.9 | Dispersible | 1 |
| | 25° C./60% RH | 11.1 | 94.0 | 3.9 | Dispersible | 1 |
| | 40° C./75% RH | 11.7 | 93.2 | 4.2 | Dispersible | 1 |

Bioactivity Assay
Study of Pharmacokinetics

3 Male rats for each group, the compound as shown in formula (I) was administered by intramuscular injection. Whole blood samples were collected at 0.25, 0.50, 1.0, 2.0, 4.0, 8.0, 12.0, 24.0 and 48.0 hour(s) after administration of the aqueous suspension group. Whole blood samples were collected at 0.25, 0.50, 2.0, 4.0, 8.0, 10.0, 24.0, 48.0, 72.0, 96.0, 120.0 and 144.0 hour(s) after administration of the oil suspension group. After precipitating the protein with acetonitrile/methanol, the supernatant was collected for sampling and the blood concentration of the compound was determined by LC-MS/MS. The non-compartment model linear logarithmic trapezoid method was used to calculate the pharmacokinetic parameters of the compounds as shown in formula (I) and formula (II) respectively by using Win-Nonlin™ Version 6.3 (Pharsight, Mountain View, Calif.) pharmacokinetic software.

Rat pharmacokinetic studies of the compound as shown in formula (I) showed that the oil suspension significantly reduced the peak blood concentration and prolonged the half-life of the drug in vivo after intramuscular administration (Table 11), thereby achieving the purpose of reducing frequency of administration and side effects while prolonging the action time of the drug in vivo, compared to the aqueous suspension (Table 10).

TABLE 10

Rat pharmacokinetics treated with the aqueous suspension of the compound as shown in formula (I) (intramuscular injection, dosage: 17.5 µM/Kg)

| Solvent formulation Compound to be tested | 25 µm/mL, 1% Tween 20, 7.5% PEG 1000, 0.75% citric acid monohydrate aqueous suspension | |
|---|---|---|
| | The compound as shown in formula (I) | The compound as shown in formula (II) |
| $C_{max}$ (nM) | ND | 438 |
| $T_{max}$ (h) | ND | 4.00 |
| $T_{1/2}$ (h) | ND | 7.52 |
| $AUC_{0-last}$ (nM · h) | ND | 5712 |
| $AUC_{0-inf}$ (nM · h) | ND | 5809 |

Note: ND means not determined (since the blood concentration was below the detection limit, the end elimination phase cannot be determined, therefore, the parameter was not determined).

TABLE 11

Rat pharmacokinetics of the oil suspension of the compound as shown in formula (I) (intramuscular injection, dosage: 51.4 µM/Kg)

| Solvent formulation Compound to be tested | 44.50 mg/mL, 0.25% Tween 80, medium chain triglyceride suspension | |
|---|---|---|
| | The compound as shown in formula (I) | The compound as shown in formula (II) |
| $C_{max}$ (nM) | 5.05 | 378 |
| $T_{max}$ (h) | 0.25 | 2.0 |
| $T_{1/2}$ (h) | ND | 24.1 |
| $AUC_{0-last}$ (nM · h) | 110.3 | 10102 |
| $AUC_{0-inf}$ (nM · h) | ND | 10351 |

Note: ND means not determined (since the blood concentration of the drug was below the detection limit, the end elimination phase cannot be determined, therefore, the parameter was not determined).

It is described in detail for the long-acting oily suspension injection of the compound as shown in formula (I) and its preparation method. While the embodiments are described in detail to help one skilled in the art to understand the present invention, but by all means the invention is not limited thereto. It will be apparent to those skilled in the art that various changes and modifications can be made therein without departing from the spirit and scope thereof.

What is claimed is:

1. A sustained release suspension containing a compound as shown in formula (I), an injectable oil and an excipient,

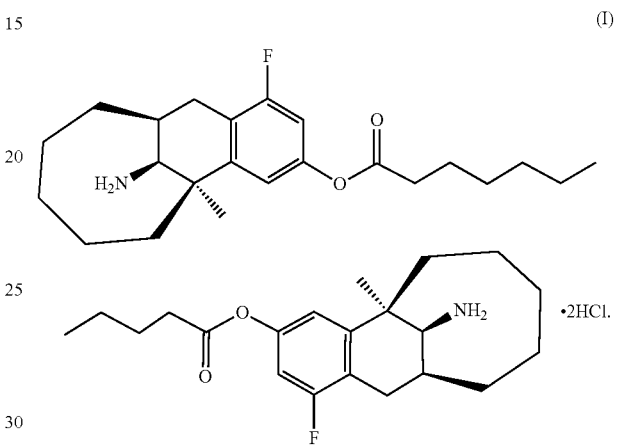

(I)

2. The sustained release suspension according to claim 1, wherein the content of the compound as shown in formula (I) is 5-20 wt. %.

3. The sustained release suspension according to claim 1, wherein the content of the excipient is 0.25-2 wt. %.

4. The sustained release suspension according to claim 1, wherein the content of the injectable oil is 80-95 wt. %.

5. The sustained release suspension according to claim 1, wherein the injectable oil is selected from the group consisting of medium chain triglycerides, soybean oil, olive oil, sesame oil, corn oil, cottonseed oil, isopropyl myristate and a mixture thereof.

6. The sustained release suspension according to claim 1, wherein the excipient is selected from the group consisting of wetting agent and suspending agent.

7. The sustained release suspension according to claim 6, wherein the wetting agent is selected from the group consisting of Tween 80, RH40, PEG400, poloxamer 188, HS-15, ethanol, propylene glycol, Span 80, polyoxyethylene hydrogenated stearate, polyoxyethylene castor oil and derivatives thereof.

8. The sustained release suspension according to claim 6, wherein the suspending agent is selected from the group consisting of methylcellulose, PVP, gelatin, sodium alginate, aluminum stearate and aluminum tristearate.

9. A method for preparing the sustained release suspension according to claim 1, wherein the method adopts a highly dispersed method.

10. The method according to claim 9, wherein the highly dispersed method is selected from the group consisting of a micronization method, an anti-solvent method, a high pressure homogenization method and a pre-suspension method.

11. The method according to claim 9, wherein 90% particle obtained according to the method is of a particle diameter≤15 µm.

12. The method according to claim 10, wherein 90% particle obtained according to the method is of a particle diameter≤15 μm.

* * * * *